US005621332A

United States Patent [19]
Inkpen et al.

[11] Patent Number: 5,621,332
[45] Date of Patent: Apr. 15, 1997

[54] DEVICE AND METHOD FOR IDENTIFYING AND QUANTIFYING LAYERED SUBSTANCES

[76] Inventors: Stuart Inkpen, Dogberry Hill Road, St. Phillips, Newfoundland, Canada, A1C 1C1; John Hall, 186 Old Topsail Road, St. John's, Newfoundland, Canada, A1B 3S6; Chris Nolan, 130 Gower Street, St. John's, Newfoundland, Canada, A1C 1P3; Chris Marshall, 50 Prescott Street, St. John's, Newfoundland, Canada, A1B 3S6

[21] Appl. No.: 411,650

[22] PCT Filed: Oct. 7, 1993

[86] PCT No.: PCT/CA93/00416

§ 371 Date: Apr. 5, 1995

§ 102(e) Date: Apr. 5, 1995

[87] PCT Pub. No.: WO94/08233

PCT Pub. Date: Apr. 14, 1994

[30] Foreign Application Priority Data

Oct. 7, 1992 [CA] Canada ................................. 2,080,067

[51] Int. Cl.$^6$ .................................................. G01R 27/02
[52] U.S. Cl. ........................................... 324/650; 364/550
[58] Field of Search ..................................... 324/650, 693, 324/632; 364/550; 244/134 F, 134 R, 134 C, 134 D; 340/580, 424.06, 962, 582; 73/178 R, 579, 583, 658, 632, 71.4

[56] References Cited

U.S. PATENT DOCUMENTS 4,628,736 12/1986 Kirby et al. ............................. 73/590
5,394,340 2/1995 Inkpen et al. ........................... 364/550

OTHER PUBLICATIONS

Measurement of Spatial Variations in Electrical Properties of Model Ice, Cold Regions Science and Technology, 16 (1989) 201–209 (Month Unavailable).

Laboratory Evaluation of a Sensor for Detection of Aircraft Wing Contaminants, 30th Aerospace Sciences, Jan. 6–0, 1992, Reno, NV, pp. 1–9.
Development of a Sensor for the Detection of Aircraft Wing Contaminants, 30th Aerospace Sciences, Jan. 6–9, 1992, Reno, NV, pp. 1–6.
An Objective Method for Measuring Surface Ice Accretion, Paul Tattelman, Apr., 1982, Air Force Geophysics Lab, Hanscom AFB, MA, pp. 599–610.
Model Approach to Obtaining Continuum Properties from Inter–Digital Electrode Dielectrometry, Mass. Institute of Technology, Jul. 1986, M. Zaretsky et al, p. 0–45.
Generation of an Aircraft Ice Sensor Data Base and Evaluation of De/Anti–Icing Fluids, Instrumar Limited, Sep., 1993, Chris Nolan et al, vol. 1 and Appendix B and C.
Evaluation of flight Crew Requirements and Human Factors Related to a Cockpit Display of Aircraft Surfaces During Periods of Freezing Precipitation, Final Report, Instrumar Limited, 12 Dec. 1994, vol. 1 and 2.
Laboratory and Field Testing of De/Anti–Icing Technologies, Instruman Limited, Feb., 1995, vol. 1.

*Primary Examiner*—Kenneth A. Wieder
*Assistant Examiner*—Barry C. Bowser
*Attorney, Agent, or Firm*—Fish & Richardson P.C.

[57] ABSTRACT

An apparatus for identifying and measuring in real time substances overlying a surface comprises a plurality of electrodes, a temperature sensor, an electrode control system connected to the plurality of electrodes for defining an electric field, an amplitude and phase measurement system connected to the plurality of electrodes and to the electrode control system for measuring a plurality of currents responsive to the electric field and converting the currents to a measurement set and computer for storing a map comprising a partition of a vector space of predetermined characteristics of substances into regions of profiles corresponding to the substances which could be overlying the surface. The computer correlates the measurement set with the map thereby identifying and quantifying the substances overlying the surface and generates an output signal corresponding to the identity and quantity of substances overlying the surface. A display responsive to the output signal displays the identity and quantity of substances overlying the surface.

11 Claims, 8 Drawing Sheets

DEVICE AND METHOD FOR IDENTIFYING AND QUANTIFYING LAYERED SUBSTANCES

FIELD OF THE INVENTION

This invention relates to a device and method for the non-intrusive and spatial interrogation of substances to identify and quantify the substances from measurements dictated by the dielectric profile of the substances. In particular, this invention relates to a device and method of detecting an accumulation of air, water, ice, snow or variety of possible contaminants such as de-icing fluid on aircraft surfaces.

BACKGROUND OF INVENTION

Ice accumulation on aircraft surfaces has been a problem since the inception of the aviation industry. The accumulation of ice has four main effects which are all negative and in some instances catastrophic. First, aerodynamic performance is severely restricted resulting in a loss of lift and increase drag. Second, the accumulation of ice increases the aircraft weight. Third, the accumulation of ice will impair or restrict the movement of control surfaces. Fourth, the ice may be ingested into the engine or other system intakes terminating engine operation.

Recently, interest in aircraft icing has been greatly heightened with an increase in industry and public awareness of the hazards associated with this problem. Although the detrimental effects of ice build up on aircraft performance has been generally well acknowledged, difficulties in predicting or measuring ice accumulation on aircraft has prevented rigorous and reliable procedures for flight crews both on the ground and in the air to minimize this problem.

The problem of aircraft icing occurs in two broad categories. First, inflight icing occurs on the leading edge of the airfoil. This type of ice build up is common and is handled by pilot observations or pilot awareness or suspicions of impending icing conditions. In many aircraft, the leading edges of the wing are heated by engine bleed air at temperatures of up to 250° C. Engine air bleed is normally done at regular intervals when icing conditions are likely regardless as to whether any ice has accumulated. A percentage of engine air is required to be used to heat the aircraft wing rather than for propulsion purposes. It is very inefficient to bleed engine air when no ice has accumulated on the aircraft surface.

The second category of aircraft icing is ground icing. Ground icing occurs over the top of the aircraft surface when the aircraft is standing. Icing on the leading 10% of the wing has the most critical aerodynamic effect. This type of ice accumulation is handled by the application of de-icing or anti-icing fluids. The problem is amplified since de-icing depends not only on how well the de-icing was undertaken but also whether ice has re-accumulated since de-icing.

On current commercial aircraft, pilots have no reliable way of judging the amount of ice accumulated on the surface of the aircraft both inflight and on the ground. Further, pilots have no means of assessing the status of the de-icing or anti-icing fluids which may have been applied in accordance with current flight procedures. Pilots are accordingly faced with difficult decisions on a regular basis in order to maintain flight schedules.

Several devices have been proposed which are designed to detect the presence of ice which has accumulated on the aircraft surface. One such device will vibrate an aircraft surface at a known frequency. When the aircraft surface vibrates at a different frequency, the presence of ice has been detected.

Still other devices have been proposed which detect the presence and thickness of ice on an aircraft surface. Such devices have been described in detail in U.S. Pat. No. 4,766,369, Weinstein. This device uses two capacitive gauges and a temperature gauge. The ratio of the voltages of sense side of the capacitive gauges determines the thickness of the ice present.

Although, these devices may detect the presence of ice on an aircraft surface it cannot detect the presence of substances other than ice such as snow, slush, de-icing fluid or din. In fact, there are no known devices which can detect the presence of snow on an aircraft surface.

Devices and analytical techniques exist for non-intrusive interrogation of materials to deduce their physical properties. Dielectric sensors and analytical techniques measure the spatial profile of permittivity of a material by multiple wavelength interrogation. A spatially periodic field is imposed upon the material via a first electrode under the control of a wavelength controller. A second or sense electrode is then used to measure the effect of the material on the charge induced by the first electrode in response to the periodic field. By varying the wavelength, spatial distribution of complex permittivity is deduced as a function of the temporal frequency. The physical properties of the material can then be deduced.

Such devices are used to monitor material changes such as the outgassing of solvents from paints, the removal of moisture from coatings, the diffusion of dopants into semiconductors and the deposition of materials. Such devices and techniques are more fully described in U.S. Pat. No. 4,814,690, Melcher, et al. and U.S. Pat. No. 5,015,951, Melcher.

Initially, it was believed that such devices and techniques would be useful in the detection of ice accumulation on an aircraft surface. However when attempts were made using such sensors to detect accumulation of ice on aircraft surfaces, the analytical techniques of Melcher, et al. were found to be highly unstable and could not in real time accurately and reliably detect, identify and measure the thickness of the various contaminants accumulating on the aircraft surface.

One of the problems of the approach of Melcher et al. is that the electric potential along a planar electrode array must be sufficiently defined and known at all times. The electric potential is required so that the theoretical models can be used to predict the spatial permittivity profile of the measured substance. However, the electric potential varies depending on the electrical properties of the substance being measured. Since the various substances which can accumulate on the aircraft surface are not known beforehand, Melcher et al., was unsuitable for use as a substance detector.

Melcher also requires sampling to be of a laboratory-quality so that the non-analyticity problems such as irregularity of the surface and complex structures could be avoided. Even with approximations, real time data processing was not possible. Data analysis using Melcher's techniques is normally in the order of hours.

Dielectric sensors measure the effects that the interrogated substance has on the capacitance of the imposed field. The problems of air gaps on dielectric sensors are well known (see U.S. Pat. No. 5,045,798, Hendrick and U.S. Pat. No. 5,095,278, Hendrick). Air gaps severely limit the sensors' ability to measure the dielectric properties since air and a vacuum have the lowest theoretically possible permittivity. Further, air also induces noise into the capacitance measurement.

SUMMARY OF INVENTION

It is therefore desirable to provide a device and method for conducting non-intrusive interrogations of substances to identify and quantify across a spatial profile, a wide range of substances in real time.

It is further desirable to provide an electrode configuration to define potential fields to provide spatial measurements by spatially varying an interrogation signal and analyzing the attenuated response thereby identifying and quantifying in real time the layered substances causing such attenuation.

In one aspect of the invention, there is provided an electrode structure which is formed by a plurality of concentric electrodes and a potential field shaper which can be implemented by electronic switches to apply a plurality of discreet voltage patterns to each electrode to define a potential field and current measurements are taken from one of the electrodes. The measurements are analyzed in real-time to identify and quantify the substances overlying the electrode.

In a further aspect of the invention, there is provided an electrode structure which is formed by a plurality of concentric electrodes and a potential field shaper which applies a discreet voltage to the electrode to define a potential field and the current measurements are taken from predetermined electrodes. The measurements are analyzed in real time to identify and quantify the substances overlying the electrode.

In a further aspect of the invention, the electrode structure can be formed by a plurality of concentric electrodes and the implied field is fixed and the measurement of the signal can be taken from different electrodes.

In a further aspect of the invention, an apparatus for identifying and measuring in real time substances overlying a surface comprises:

a sensor head comprising a protective layer having a top surface, an electrode layer having a plurality of electrodes imbedded therein, a backing layer having temperature sensors for generating a signal dependent on temperature and a ground plane layer, connector pins extending from the plurality of electrodes and the temperature sensor through the backing layer and insulated from the ground plane layer, a grounding pin for grounding one electrode to the ground plane layer, the layers integrally moulded together, an electrode control system connected to the plurality of electrodes for defining an electric field at the top surface, the electric field approximating a Bessel function, an amplitude and phase measurement system connected to the plurality of electrodes and to the electrode control system for measuring the currents responsive to the electric field and convening the current response to a measurement set comprising at least seven dimensional regions defined by three complex measurements of impedance and temperature, and computer means for storing a map means comprising a partition of a vector space of predetermined characteristics of substances into regions of profiles corresponding to the substances which could be overlying the surface, said computer means for correlating the measurement set with the map means thereby identifying and quantifying the substances overlying the surface and for generating an output signal corresponding to the identity and quantity of substances overlying the surface, and display means responsive to the output signal for displaying the identity and quantity of substances overlying the surface.

In still yet another aspect of the invention, a second computer means stores a database comprising sample data of sample measurements of the probable substances and quantities thereof together with estimates of corresponding profiles of the sample data and theoretical data of the probable substances and quantities thereof together with corresponding profiles of the theoretical data, the second computer means remote from said first computer means, the map means is generated by a second computer means by (a) selecting the probable substances which are likely to be overlying the surface, (b) selecting data from the database corresponding to the probable substances, (c) successively dividing the selected data into subsets until each subset satisfies a predetermined criteria for subdividing;

(d) defining a set of boundary functions, each of which describe a hierarchial boundary between the subsets;

(e) defining a set of profile functions, each of which describe the distribution of the data in each subset; and (f) collecting the sets of boundary and profile functions in a map means.

In still yet another aspect of the invention, the computer correlates the measurement set with the generated map means by (a) defining a local profile by applying the measurement set to the map means, (b) refining the local distribution by numerical dithering of the measurement set, (c) calculating the variation of the refined local distribution, (d) comparing the variation with a predetermined limit and if the variation is greater than a predetermined limit, sending the output signal that the substance has not been identified and if the variation is less than or equal to the predetermined limit sending the output signal corresponding to the identity and quantity of the substances detected.

In still yet another aspect of the invention, there is provided a method for identifying and measuring substances overlying a surface using a plurality of concentric electrodes underlying a surface, an electrode control means connected to the plurality of electrodes for defining an electric field at the surface, an amplitude and phase measurement means connected to the plurality of electrodes and electrode control means for measuring the currents responsive to the electric field, computer means for storing a map means comprising a partition of a vector space of predetermined characteristics of substances into regions of profiles, and a display means responsive to an output signal for displaying the identity and quantity of substances overlying the surface. The method comprising the steps of:

(a) applying an electric field at the surface, (b) measuring currents responsive to the electric field, (c) converting the currents to a measurement set, and (d) defining a local profile by applying the measurement set to the map means, (e) refining the local distribution by numerical dithering of the measurement set, (f) calculating the variation of the refined local distribution, (g) comparing the variation with a predetermined limit and if the variation is greater than a predetermined limit, sending the output signal that the substance has not been identified and if the variation is less than or equal to the predetermined limit sending the output signal corresponding to the identity and quantity of the substances detected;

(h) generating an output signal corresponding to the identity and quantity of substances overlying the surface; and (i) after a fixed period of time, repeating the process.

According to yet another aspect of the invention, a method of generating a map is provided by (a) selecting the probable substances which are likely to be overlying the surface, (b) selecting data from a database corresponding to the probable substances, said database comprises sample data of sample measurements of the probable substances and quantities thereof together with estimates of corresponding profiles of the sample data and theoretical data of the probable substances and quantities thereof together with corresponding profiles of the theoretical data, (c) successively dividing the selected data into subsets defining a set of boundary functions describing hierarchial boundaries between the subsets, the subsets being divided until each subset satisfies a predetermined criteria for subdividing, (d) defining a set of profile functions describing the distribution of the data in each subset;

(e) collecting the set of boundary and profile functions in a map.

DETAILED DESCRIPTION OF THE DRAWINGS

In drawings which illustrate embodiments of the invention.

DETAILED DESCRIPTION OF THE INVENTION

The underlying physics governing the functional performance of the device of the present invention are based on the electroquasistatic subset of Maxwell's equations:

$$\nabla \cdot \epsilon E' = \rho'$$

$$\nabla \times E' = 0$$

$$\nabla \cdot \sigma \underline{E} + \frac{\partial \rho'}{\partial t} = 0$$

where the variables are defined as follows:
E' electric field intensity
ρ' free charge density
ε absolute permittivity
σ conductivity For purposes of illustration, the material under study is approximated by horizontal layers (parallel to the sensor) in which the electrical properties are constant, and that all primed quantities vary as $e^{j\omega t}$ (where j is the square root of −1, ω is the angular frequency of excitation, and t is the time) allows the reduction of the above system to the determination of a Laplacian potential, Φ, within any given layer to the scalar equation:

$$\nabla^2 \Phi = 0$$

where $$-\nabla \Phi = E$$

At a boundary between layers the following jump conditions hold:

$$\|\Phi\| = 0$$

$$\left\| \underline{\epsilon} - \frac{\partial \Phi}{\partial n} \right\| = 0$$

where $\underline{\epsilon} = \epsilon - \sigma/j\omega$ and $\underline{n}$ is the unit vector normal to the potential.

For a cylindrically concentric electrode embodiment the problem is cylindrically symmetric normal to the sensor surface. The potential function is decomposed into the natural eigenfunctions:

$$\Phi(r, z) = \sum_m \Phi_m(z) J_o(\lambda_m r)$$

where $J_o(\lambda_m r_o) = 0$, $J_i$ is the ith Bessel function, z is the coordinate normal to the sensor surface, r is the radial distance from the original, and $r_o$ is chosen large enough so that the potential is essentially zero beyond it.

These equations are then solved to yield an expression for the ideal charge density, and hence the current, on the surface of the electrode. This is only an approximate solution as the electric potential between the electrodes has not been specified.

For a structure consisting of k finite layers bounded away from the sensor by an infinite uniform material (i.e. the atmosphere), the current on an electrode of inner and outer radii $r_1$ and $r_2$ respectively is given by:

$$I = 2\pi j \omega \epsilon_1 \sum_m \{\Phi_m(0) L_{m,n}(r_2 J_1(\lambda_m r_1) - r_1 J_1(\lambda_m r_1))\}$$

where for n<k+1 we have:

$$L_{m,n} = -\coth(\lambda_m \Delta_n) + \frac{1}{\sinh(\lambda_m \Delta_n)^2 \left( \coth(\lambda_m \Delta_n) - \frac{\epsilon_n + 1}{\epsilon_n} L_{m,n+1} \right)}$$

while $L_{m,k+1} = -1$ and $\Delta_n$ is the thickness of the nth layer.

The actual measurements are made in the form of impedances, or equivalently, as admittances (the reciprocal of impedance). The model must also account for the contribution to the total admittance of each pattern made by the fields generated by the support electronics. Because this contribution is independent of the material above the sensor, the total admittance can be written as:

$$A_{total} = \frac{I}{P} + A_{strays}$$

where P is the potential on the sensing electrode and $A_{strays}$ is the contribution from the support electronics.

Figure 1:
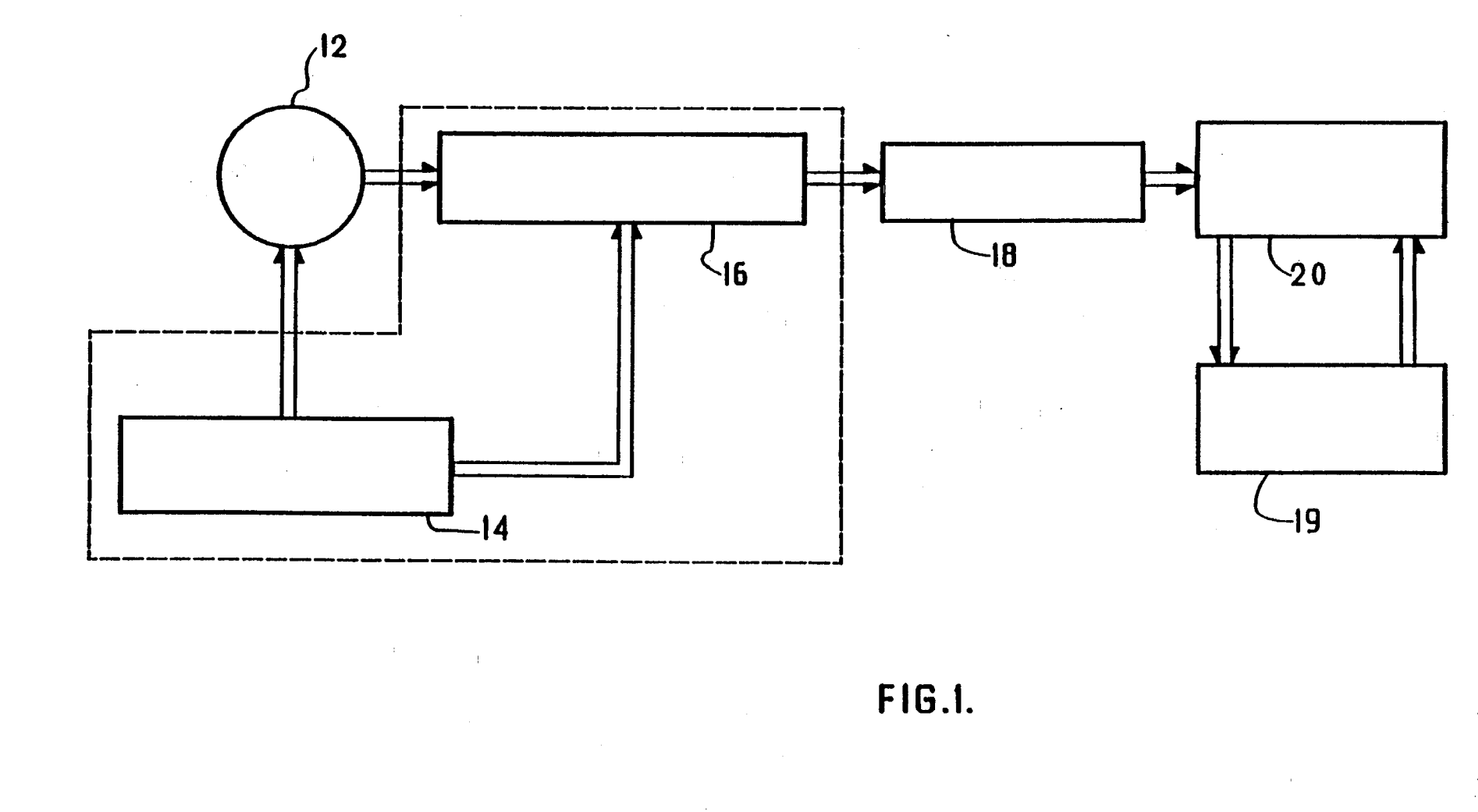
FIG. 1 is a block diagram of the preferred embodiment of the invention.

The device of the present invention is schematically illustrated in FIG. 1. The invention generally comprises a sensor head 12, electrode control 14, amplitude and phase measurement system 16, communications systems 18 and computer and output display system 20. Preferably, computer 20 is at least a computer having an INTEL 286 or equivalent processor using standard RS232 connections and the display is a conventional monitor.

Figure 2:
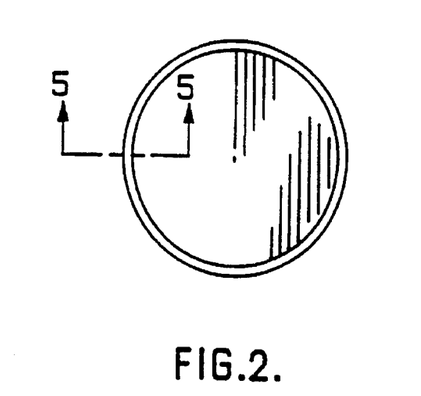
FIG. 2 is a top plan view of the sensor head of embodiment of FIG. 1.
Figure 3:
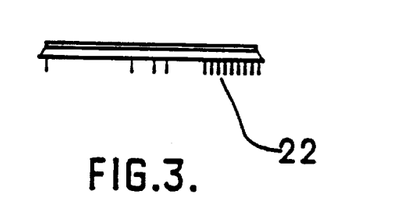
FIG. 3 is a side elevational view of the sensor head of FIG. 2.

Referring to FIGS. 2 and 3, sensor head 12 of the preferred embodiment has a circular outline in plan view and a slim profile. Extending below the sensor head 12 is a plurality of connector pins 22.

Figure 4:
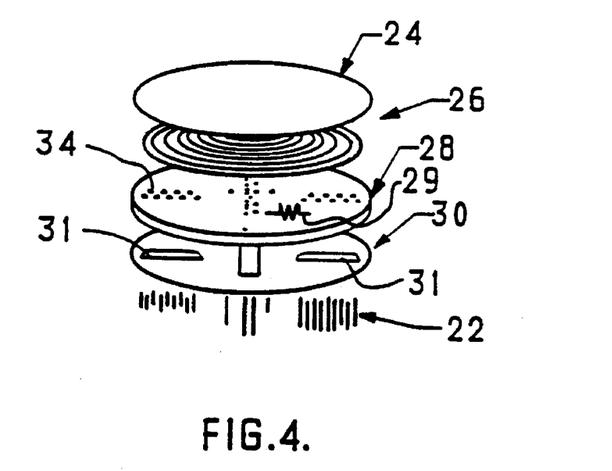
FIG. 4 is an exploded view of the sensor head of FIG. 2.
Figure 5:
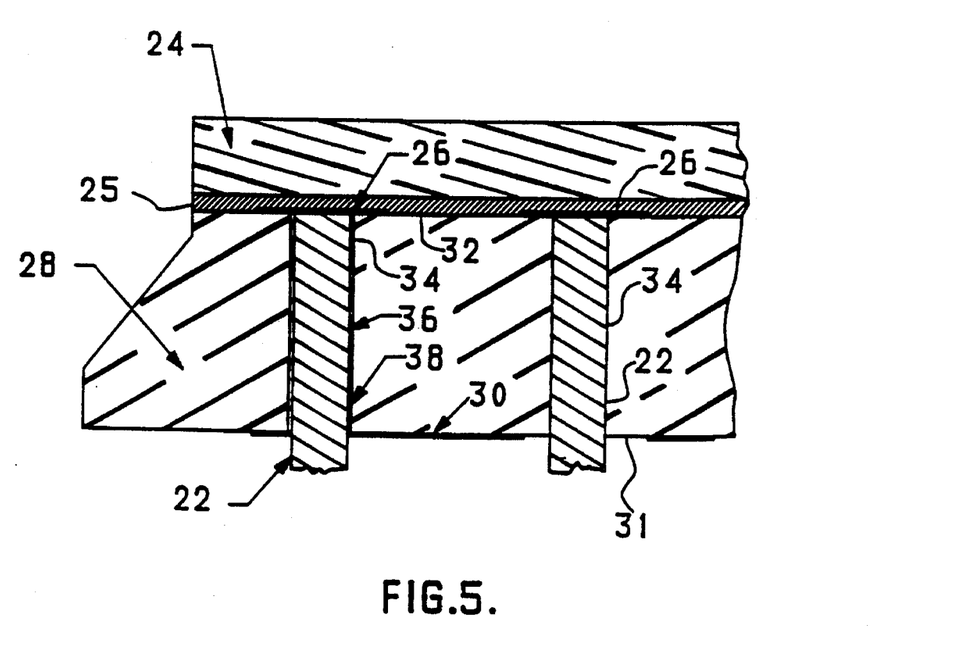
FIG. 5 is partial side sectional view of the sensor head of FIG. 2 along the lines 5—5.

The construction of sensor head 12 is illustrated in detail in FIGS. 4 and 5. The sensor head has a protective layer 24 on the top surface. Immediately below the protective layer 24 is electrode layer 25 having imbedded therein electrodes 26. Below the electrode layer 25 is backing layer 28. On the bottom surface is a ground plane layer 30. A temperature sensor or thermistor 29 is embedded in backing layer 28. Thermistor 29 is electrically connected to a pair of connector pins for external connection. Thermistor 29 allows temperature measurements to be taken.

Protective layer 24 and backing layer 28 are preferably made of beryllium oxide. Beryllium oxide has a high thermal conductivity which is similar to aluminum and is electrically insensitive to temperature. Other materials could be used provided such material has good thermal conductivity, is electrically insulating and is electrically insensitive from at least –55° to 86° C. but preferably between –65° to 100° C.

The electrodes 26 are embedded in electrode layer 25 in an epoxy or a glass substance 32. A plurality of bores 34 extend axially through backing layer 28. In the preferred embodiment, the configuration of electrodes 26 is a plurality of concentric circular electrodes.

As noted in detail later, this configuration can be represented in cylindrical coordinates and the resulting voltage pattern can then be transformed mathematically by a Bessel series. The cylindrical configuration allows the voltage pattern to be represented in one dimension because the voltage level along the electrode plane is independent of angular position and only dependent on the radial position from the centre.

The number and width of the electrodes and the radial separation are governed by the maximum allowable size of the sensor, the maximum accretion thickness that must be detected, and the required sensitivity and accuracy of the measurements.

The penetration depth of the electric field from the sensor depends on the distribution of spatial wavelength information at the electrodes. Different electrode configurations can be obtained to concentrate measurement sensitivity at desired depths in the substance being sensed. The sensitivity of a given configuration can be optimized by selecting a configuration that will maximize the energy from the desired spatial component. A great number of electrodes will facilitate increased flexibility in the selection of optimum configurations.

Connector pins 22 extend through the bores 34 and are in electrical contact with the electrode rings 26. Ground plane layer 30 has a plurality of openings 31 allowing connector pins 22 to be insulated from contact therewith.

In the preferred embodiment, the outermost ring of electrodes 26 is grounded. The inside surface of the outermost of bores 34 has a metallized surface 36. The outermost of connector pins 22 is brazed to the metallized surface 36 to form a hermetic joint 38.

As illustrated schematically in FIG. 1, sensor head 12 is electrically connected through connector pins 22 to electrode control 14 and amplitude and phase measurement system 16.

Figure 6:
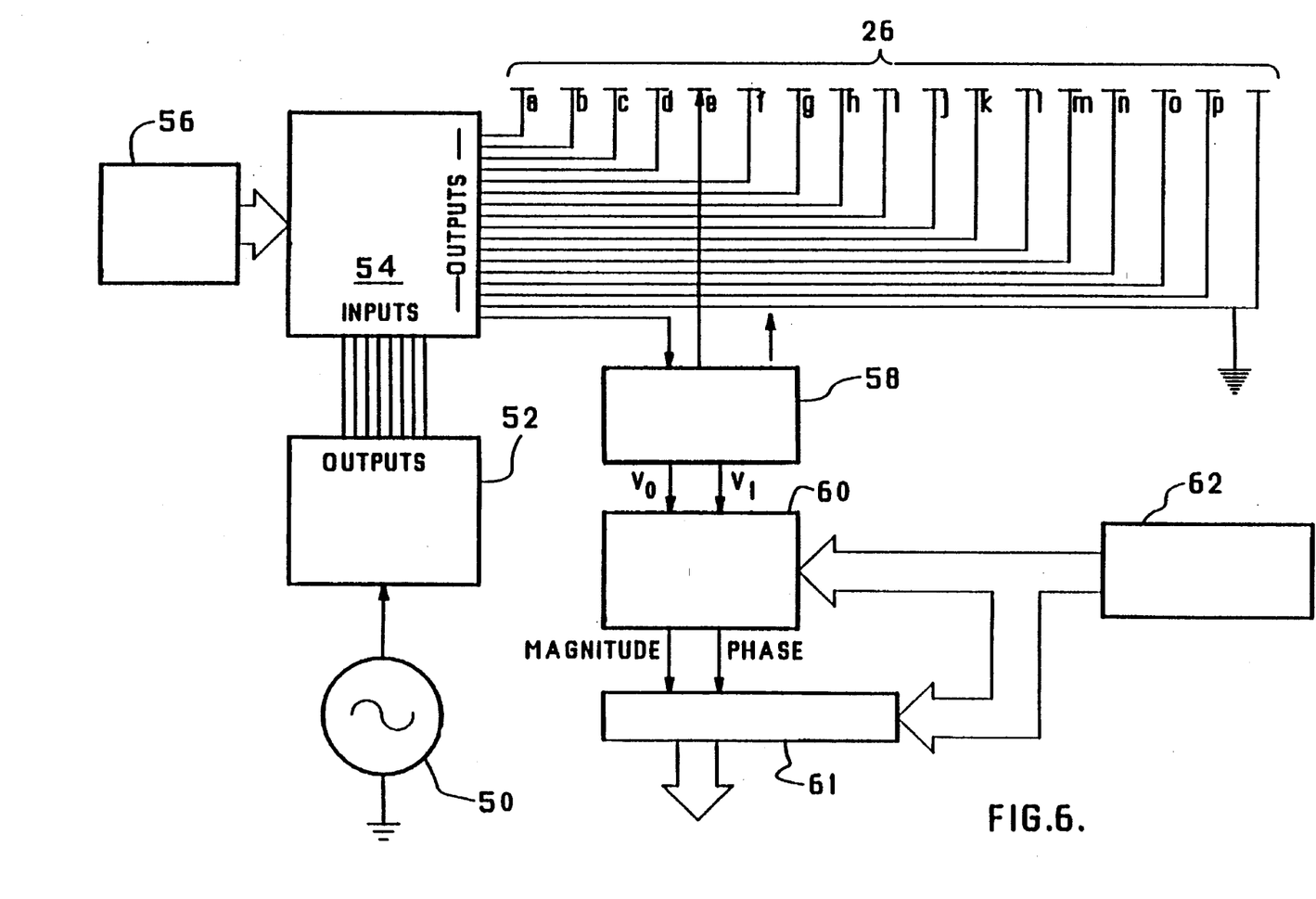
FIG. 6 is a block diagram of the embodiment of FIG. 1, illustrating an electrode structure of concentric rings.

Electrode control 14 is schematically illustrated in FIG. 6. Electrode control 14 comprises a signal source 50 connected to a multiple voltage generator 52. The multiple voltage generator feeds a signal selector 54. A digital pattern control 56 also feeds the signal selector 54 to determine the voltage that is applied to each electrode. Each of the outputs of the signal selector 54 are connected in parallel to each ring of the electrodes 26, with the exception of ring e. Ring e is fed directly from sense circuit 58. Signal selector 54 also feeds sense circuit 58 which in turn feeds ring e.

The amplitude and phase measurement system 16 comprises a sense circuit 58, a vector voltage measurement circuit 60 and digitization 61. Sense circuit 58 is responsive to signal selector 54 and applies both the input voltage to ring e and monitors the resulting current in ring e. Sense circuit 58 will output two signals which are representations of the applied voltage and the resulting current. The two signals are fed to the vector voltage measurement circuit 60 that produces voltage levels which correspond to the magnitudes and relative phase of the two signals. Digitization 61 digitizes the two signals into a digital format and delivers the digitized signals to communications system 18.

The communications system 18 comprises a digital measurement control circuit 62 which is a microprocessor based control. The digital measurement control 62 controls the pattern generation and measurement sequences. It also controls the calibration and monitoring routines and formats the data for outputting to the computer 20.

Figure 9:
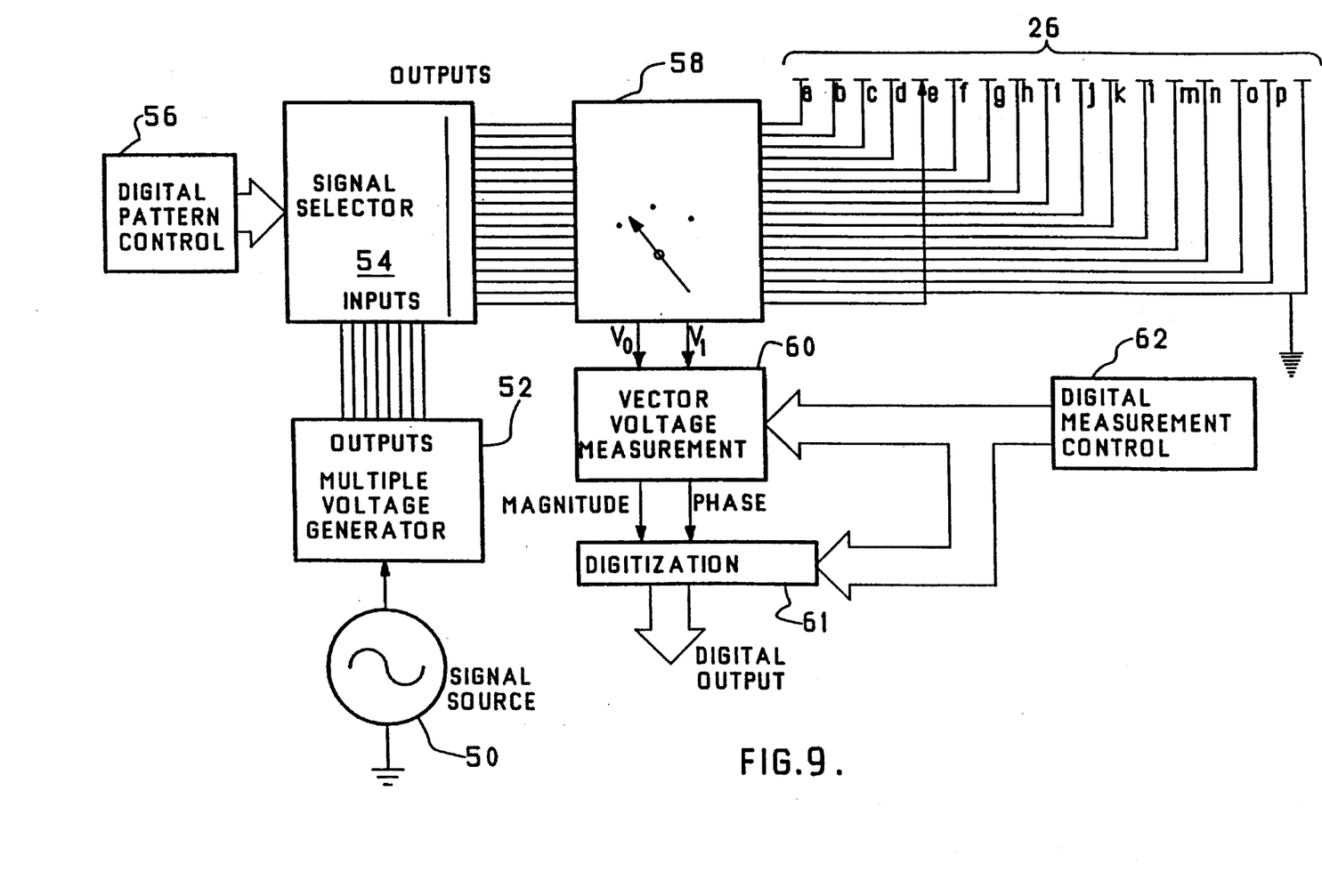
FIG. 9 is a block diagram of a second embodiment of FIG. 1, illustrating an electrode structure of concentric rings.

The circuits illustrated in FIGS. 6 and 9 are known standard electronic circuits. The circuits are electrically connected in a conventional manner to achieve the desired results.

The electrode control 14 can operate in one of two ways. Both ways provide equally satisfactory results. Referring to FIG. 6, the electrode control 14 could successively apply several discrete voltage patterns to the electrodes 26 to define a series of potential fields. Only one designated electrode of electrodes 26 is used to measure the resulting currents. Alternatively, as illustrated in FIG. 9, the electrode control 14 could be fixed and apply only one discrete voltage pattern. The measurements are taken from alternately switched electrodes. In either case, a resulting series of currents from the sensor head 12 is obtained.

The discrete voltage patterns or electrode configuration can be specialized to sense material at specific layer thicknesses. For example, the measurement obtained by one voltage pattern or electrode configuration could be most sensitive to material within a 1 mm thickness while other configuration is sensitive to layer thicknesses of up to 5 mm.

Figure 7:
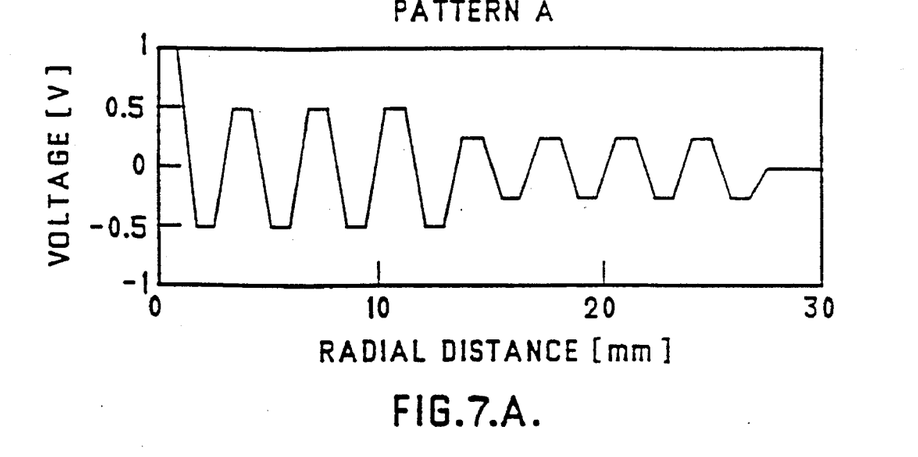
FIG. 7A–C are the applied voltage patterns of the embodiment of FIG. 1.

In the preferred embodiment, the voltage patterns represent Bessel functions. Three distinct patterns as illustrated in FIG. 7 can be used. Each discreet voltage pattern vary sinusoidally with time at a fixed magnitude and phase. For detection of substances which are likely to be found on an aircraft surface, a sinusoidal frequency of 1 MHz has been found to be suitable. The three patterns differ in the initial period and the rate of decrease in period.

Each configuration creates an electric field that produces a current in the electrodes. The magnitude and phase of this current depends on the electrical characteristics and the thickness of the substance present on the sensor surface. The sensitivity of each configuration to the material being measured decays exponentially as a function of its depth. Each measurement configuration has a different rate of decay that is characterized spectrally by its dominant spatial wavelength such that the degree of penetration is intentional and unique to each.

Referring to FIG. 6, sensor head 12 is schematically illustrated having a plurality of concentric electrode rings 26 a–p. Each ring is electrically connected to the electrode control 14. Ring e is electrically connected to the amplitude and phase measurement system 16. The electrode control 14 applies a voltage pattern to each of the concentric electrode rings. The amplitude and phase measurement system 18 will measure the responsive current from a designated one of the concentric electrodes 26, ring e.

The electrode control 14 establishes and switches between each configuration of FIG. 7. Sense circuit 58 measures the three resultant currents imposed in the designated one of the electrodes 26, ring e. Each of the resultant currents is successively digitized to form six data inputs. A temperature measurement is taken from thermistor 29 and the seven pieces of data will form a measurement set. The measurement set is transferred from the amplitude and phase measurement system 16 to the communications system 18 to the computer 20 for processing using the inversion software.

Communications system 18 can be any suitable form of data transmission. The resultant current received from the amplitude and phase measurement 16 is in an analog format. Communications system 18 can either transmit the data in an analog format and convert to a digital format prior to final transmission to the computer 20. Preferably, the data is converted immediately into digital and transmitted in a digital format to computer 20.

For use as an substance detector, the sensor head 12 is installed in a wing or tail surface of an aircraft. The remaining hardware of the system can be installed in the main body of the aircraft with electrical connections extending between the sensor head and hardware. The display can be mounted in the cockpit for easy review by the pilot or other flight officer.

The sensor head should be placed on the leading 10% of the wing or tail surface. This will allow the sensor to detect inflight icing, yet will be sufficiently level for accurate ground ice monitoring. In most commercial aircraft this will permit the installation of the sensor head 12 behind the bleed air heated region and in front of the fuel tank. At this point, the curvature of the wing is sufficiently small to allow the sensor head 12 to have a 60 mm diameter to fit inconspicuously and with no significant change in wing geometry. The sensor head 12 should be mounted flush to the wing surface to present a minimal disturbance to the air flow.

When the preferred embodiment is used in an aircraft, government regulations require that the sensor head 12, the electrode control 14, the amplitude and phase measurement 16 and communications system 18 meet the emissions requirements outlined in FCC Part 15, Subpart B Class A, 15.107(a) (Conducted Emissions) and 15.109(a) (Radiated Emissions). Further, the sensor head 12 should be in conformance with MIL-STD-461C, RS03, as well as other standards as may be applicable.

In very general terms, a measurement set is generated by the sensor head and transferred to computer 20. The analytical software within computer 20 then approximates the profile of the physical structure of the substances overlying the sensor head 12. Artificially intelligent inversion routines incorporating previously measured and theoretical material signatures are able to identify substances and their thickness given the sensed currents.

Referring to FIG. 1, the analytical techniques will be described in detail. The computer of the present invention comprises a ground computer 19 and an on-board computer 20. The ground computer 19 creates, stores and manages a main database which is used to create a map which is used to transform a measurement set of data into a profile. Optionally, the ground computer can have the capability of simulating the on-board computer 20.

The ground computer 19 stores a sample database 66 containing archived controlled measurements. Initial sample measurements are taken on relatively simple configurations. For example, the sample measurements may generate data for scattered droplets, uneven mixing, irregular layering, contamination and variations due to local and environmental factors. These sample measurements are indexed and stored together with the estimates of their corresponding profile.

The main database also includes theoretical database 68 which enhances the sample database 66 by using theoretical models to fill in the gaps between the measured data. The theoretical set of data is created from theoretical models. For example, the theoretical set may generate data for mixtures and layers of water and de-icing fluid. The theoretical set is stored together with the estimates of their corresponding profiles.

For implementation of the system as a substance detector, the probable substances which can be expected to overlay the sensor head are identified, such as air, ice, snow, slush, dirt, water and de-icing or anti-icing fluids. The data relevant to the probable substances is then extracted from the main database by interpretation function 70. The data is transformed into a set of vectors which define the vector space.

The vector space is reorganized and broken down into two subsets of subregions with less variation than the parent set. An estimate of the potential for further subdivision is calculated and stored as well as a boundary function of the hyperplane dividing the subregions. The hyperplane will determine a hierarchial boundary dividing the various regions of the vector space. If a predetermined criteria regarding the separability of data is not satisfied, a profile function is created describing the distribution of profiles in that region.

If predetermined criteria regarding the separability of data is satisfied, the next region which has the highest potential for subdividing is then selected and subdivided into two further subregions. The process of subdividing is repeated until no region of sufficient potential for subdividing exists.

A map of the regions of the vector space is thus created by collecting a set of boundary functions describing the hierarchial boundaries and a set of profile functions describing the distribution of profiles in each region. In other words, the map is a partition of the vector space into regions corresponding to known profiles, regions of unknown substances and regions corresponding to functions for building profiles of known substances. The map also includes a predetermined limit on the variation of the corresponding profile.

Only the map is loaded into the on-board computer 20. The memory requirements of the on-board computer 20 is greatly reduced in comparison to the requirements of the ground computer 19 which stores the entire main database. This permits the on-board computer 20 to be a conventional personal computer with an INTEL 286 or equivalent processor. By using a map rather than a database, the speed at which substances can be identified is greatly enhanced. Substances can be identified in real-time to substantially instantaneous identification and quantification.

In use, a raw measurement set of data from the sensor head 12 is generated depending upon the substances overlying the sensor head 12. The raw measurement set is corrected for temperature variations. The measurement set is then transformed into a test vector of predetermined characteristics. The predetermined characteristics are in terms of a seven dimensional test vector defined by three complex measurements of impedances (or inversely admittances) and temperature. Optionally, time may be included as an eighth dimension to analyze evolving materials such as degrading de-icing fluids. Further extensions to any arbitrary number of dimensions can be made using non-linear independent combinations of primary basis elements.

The computer 20 must "decide" whether the test vector matches any one of the regions in the vector space. The interpretation routine 64 applies the test vector to the map by first applying the test vector to the set of boundary functions. The result identifies a small number of possible configurations for the substance overlying the sensor. The interpretation routine 64 then specifically identifies the region in which the test vector falls by comparing where the test vector exists in relation to the hierarchial boundaries. Once the interpretation routine 64 identifies the region of the vector space, the local function of the set of profile functions is executed to determine the local profile.

Any electrical instrument is subject to a certain degree of electrical noise. It is important to lessen the effect of this noise might have on the determination of a final result.

In order to provide a stable estimate of the true profile overlying the sensor head 12, small amounts of random numerical noise is added to the measurement set generating another test vector. The process of applying the test vector to the map is repeated. This step is known as dithering. Dithering is used to lessen any dependence of the measurement set which may exist on the inherent electronic noise. Generally, eight to sixteen passes have been found to be satisfactory. The number of passes is restricted to an integral power of two in order to reduce the averaging procedure to a simple bit shift.

The profiles generated by the numerical dithering are combined to a single profile. The variation of the profile is used to weight the single profile. The variation also provides an estimate of the reliability of the measurement set. If the variation is greater than the predetermined limit, the substances overlying the sensor head 12 has not been identified. If less than or equal to the predetermined limit, the substance overlying the sensor head has been identified and quantified. The variation will also reflect the certainty of the identification.

If the substances overlying the sensor head has been identified and quantified, the measurement set is stored in a memory together with the corresponding interpretation of the measurement set. Periodically, the stored data may be downloaded to the ground computer to be added to the main database. When data has been collected in such manner, its interpretation can be corrected, with respect to materials and structure, by an "expert" user at 74. In this manner, artificially intelligent routines can be used to enhance the quality of the map which can be generated.

The creation and maintenance of the map and the operation of the invention are described in further detail. A map means for installation into the interpretation routine 64 is created by the following steps:

(a) identifying the probable substances which are likely to be overlying the surface, such as air, ice, snow, slush, dirt, water and de-icing or anti-icing fluids, (b) selecting data in a vector format from the database corresponding to the probable substances defining a vector space, (c) dividing the selected data into subsets or subregions of the vector space defining boundary functions describing the hierarchial boundaries between the subsets, defining a profile function describing the distribution of the data in each subset;

(d) subdividing the selected data until each subset satisfies predetermined criteria for subdividing;

(e) collecting the set of boundary and profile functions in a map.

The map can then be loaded into the interpretation routine 64. The analysis of a measurement set of the resulting currents is carried out in the following steps:

(a) A raw measurement set is input to the on-board computer 20 from the sensor through communications system 18. The measurement set includes three complex impedances in magnitude and phase form, temperature information, and optionally time.

(b) The raw measurement set is calibrated by temperature calibration 72, and convened to a vector format for input to the interpretation routine 64.

(c) The local profile corresponding to the measurement set is determined by applying the measurement set to the map means.

(d) The local profile is refined by numerical dithering of the measurement set. Reliability is tested by calculating the variation of the refined local profile.

(e) If the variation is greater than the predetermined limit, the substances overlying the sensor head has not been identified. If less than the predetermined limit, substance overlying the sensor head has been identified and quantified. Actions to be taken, such as signalling alarms, are effected.

(f) If the substances overlying the sensor head has been identified quantified, the measurement set is stored in a memory together with the corresponding profile of the measurement set. Periodically, the stored data process may be downloaded to the ground computer to be added to the main database.

The operation of the invention may be described in terms of the following example. The three patterns A, B and C of FIG. 7 are applied to a sensor head. Overlying the sensor head is a sample of snow at $-5°$ C. The current from ring e is the input to sense circuit 58. Sense circuit 58 amplifies the current and converts the input current to a voltage. The output of the sense circuit 58 is as follows:

| PATTERN | MAGNITUDE $V_1$ [mV RMS] | MAGNITUDE $V_0$ [MV RMS] | PHASE [DEG] |
|---------|--------------------------|--------------------------|-------------|
| A | 480.08 | 118.381 | −40.88 |
| B | 480.20 | 159.604 | −35.98 |
| C | 480.32 | 207.725 | −30.07 |

These values are transferred to the vector voltage measurement circuit 60. Voltage measurement circuit 60 converts the sinusoidal signal to a DC type signal. The voltage measurement circuit then scales the voltage values to a voltage between 0 and 10 volts. The output of circuit 60 is as follows:

| PATTERN | MAGNITUDE (V) | PHASE (V) |
|---------|---------------|-----------|
| A | 2.04090 | 7.28814 |
| B | 2.75158 | 6.79767 |
| C | 3.58120 | 6.20749 |

These values are then digitized in digitization circuit 61. The output of digitization is as follows:

| PATTERN | MAGNITUDE | PHASE |
|---------|-----------|-------|
| A | 0.246586 | −40.8814 |
| B | 0.332369 | −35.9767 |
| C | 0.432472 | −30.0749 |

The input voltage patterns A, B and C vary with respect to time in a fixed magnitude and phase. Accordingly, the measurements are taken over a period of time to obtain minimum and maximum values and average values. In the preferred embodiment, a time period of 30 ms is used. The time period should be sufficiently short to avoid fluctuation problems with changing physical conditions on the sensor surface. A full set of sample data from the sensor head is a set of 27 real numbers, in ASCII format. The following table is a sample reading taken of air at 24° C.:

| PATTERN | PROPERTY | AVERAGE | MINIMUM | MAXIMUM |
|---------|----------|---------|---------|---------|
| A | Magnitude | $2.423037 \times 10^{-1}$ | $2.418614 \times 10^{-1}$ | $2.427494 \times 10^{-1}$ |
| A | Phase | $-4.135507 \times 10^{1}$ | $-4.124039 \times 10^{1}$ | $-4.144810 \times 10^{1}$ |
| A | Temperature | $2.428713 \times 10^{1}$ | $2.425604 \times 10^{1}$ | $2.430692 \times 10^{1}$ |
| B | Magnitude | $3.281975 \times 10^{-1}$ | $3.277824 \times 10^{-1}$ | $3.286453 \times 10^{-1}$ |
| B | Phase | $-3.652611 \times 10^{1}$ | $-3.642485 \times 10^{1}$ | $-3.658522 \times 10^{1}$ |
| B | Temperature | $2.427846 \times 10^{1}$ | $2.425604 \times 10^{1}$ | $2.429613 \times 10^{1}$ |
| C | Magnitude | $4.272364 \times 10^{-1}$ | $4.267879 \times 10^{-1}$ | $4.278819 \times 10^{-1}$ |
| C | Phase | $-3.064128 \times 10^{1}$ | $-3.057229 \times 10^{1}$ | $-3.072710 \times 10^{1}$ |
| C | Temperature | $2.427653 \times 10^{1}$ | $2.424371 \times 10^{1}$ | $2.429459 \times 10^{1}$ |

The data is convened to machine code (ASCII format) and a simple check is carried out to assess whether the data has been corrupted by signal noises or other sources. The average value of the data is compared against the corresponding minimum and maximum values. If the result indicates that the data is valid, each set of magnitude and phase values are converted from an impedance to an admittance.

The data is next calibrated to remove any dependence of the data on temperature and to correct for any long term drift in the electronics. The temperature coefficients $T_0$ and $T_1$ are created by operating a clean sensor in a temperature controlled environment. The sensor should be independent of temperature. The variations in readings can then be calibrated such that the readings remain constant. The temperature coefficients $T_0$ and $T_1$ are stored within the sensor evaluation software. The drift calibration term A can be generated when required by assuming an air reading and a DATA VALUE of zero.

$$A[n]=SAMPLE[n]-T_0[n]-T_1[n] \times T$$

where T is the temperature in °C.

The following is a table of typical calibration values:

| PATTERN | $T_0$ [n] | $T_1$ [n] | A [n] | [n] |
|---------|-----------|-----------|-------|-----|
| A real | $3.067681 \times 10^{0}$ | 0.002285318 | −0.003745 | 0 |
| A complex | $2.660739 \times 10^{0}$ | 0.002160601 | −0.004497 | 1 |
| B real | $2.428113 \times 10^{0}$ | 0.001389255 | −0.002961 | 2 |
| B complex | $1.767522 \times 10^{0}$ | 0.001398589 | −0.003790 | 3 |
| C real | $1.999283 \times 10^{0}$ | 0.0009045687 | −0.002560 | 4 |
| C complex | $1.160502 \times 10^{0}$ | 0.0009285227 | −0.002965 | 5 |

Applying these calibration factors to the raw data, yields the following set of data:

| PATTERN | SAMPLE VALUE | DATA VALUE | [n] |
|---------|--------------|------------|-----|
| A real | 3.066131 | 14 | 0 |
| A complex | 2.654228 | 9 | 1 |
| B real | 2.434807 | 17 | 2 |
| B complex | 1.767481 | 11 | 3 |
| C real | 2.000989 | 9 | 4 |
| C complex | 1.158763 | 6 | 5 |

The DATA VALUE is obtained from the SAMPLE VALUE by applying the calibration and scaling factors as follows:

$$DATA[n]=1024 \times (SAMPLE[n]-A[n]-T_0[n]-T_1[n] \times T)$$

where T is the temperature in °C.

The temperature is increased by a factor of 10 to account for a decimal place in the temperature reading and to keep the temperature in an integer format. The results of the DATA VALUE is combined with temperature and a unit element. The unit element is a constant which will ensure that the inner product comes out as either a positive or negative value. The resultant test vector is as follows:

$$V=[14,9,17,11,9,6,-50,1]$$

The next step in the process is the mapping of the test vector to a region of the vector space. This is carried out by building up a number of profiles using the dithered values in the test vector and then combining them to present a final profile.

A major profile M is a two dimensional matrix whose numbers of rows equal that of the number of possible materials to be tested and which has 128 columns, each of which corresponds to a material layer one tenth of a millimeter thick. The major profile M is initialized to contain all zeros.

A minor profile m is initialized in the same manner, except that a "guess" is made as to the material overlying the sensor head. This can be represented in the following table, assuming the first guess is air and the first eight tenths of a millimeter:

| unknown | 0 | 0 | 0 | 0 | 0 | 0 | 0 | 0 | — |
|---|---|---|---|---|---|---|---|---|---|
| air | 15 | 15 | 15 | 15 | 15 | 15 | 15 | 15 | — |
| snow | 0 | 0 | 0 | 0 | 0 | 0 | 0 | 0 | — |
| ice | 0 | 0 | 0 | 0 | 0 | 0 | 0 | 0 | — |
| water | 0 | 0 | 0 | 0 | 0 | 0 | 0 | 0 | — |
| de-icing fluid | 0 | 0 | 0 | 0 | 0 | 0 | 0 | 0 | — |

The numerical values in the table indicate a measure of certainty, with 0 being the least and 15 being the highest.

The map describing the vector space consists of a series of data structures. Each structure contains a variety of digital information. The information may include a numerical description of a boundary between the regions divided, an instruction for correcting the current profile estimate, a means to estimate the validity of the test vector, and indices to the next level of decision.

The numerical description of a boundary is in form, a test vector. Mathematically the vector describes the hyperplane separating two regions of the vector space. The inner product of boundary B and the current dithered test vector D, B·D yields an integer value whose sign indicates which region for examination is to be chosen and whose signed value is used to determine the validity of the interpretation.

Returning to the example of the snow reading, the hyperplane boundary between high permittivity materials such as water or de-icing fluid and low permittivity materials such as ice, snow could be as follows:

$$B=[143,78,52,63,25,30,0,-3762]$$

The inner product yields $$B \cdot D = 1136 > 0$$

indicating that the positive branch data structure should be the next chosen. In other words, the inner product indicates that the assumption that the sensor is clean is wrong.

This choice is conditional upon the acceptance of the inner product value at the next level. Each branch of the tree maintains an expected value for the inner product result from the previous level together with minimum and maximum expected deviations for this value. Should the inner product value fall outside this range, the construction procedure is terminated. By terminating the procedure, the minor profile now represents an estimate of the distribution of all profiles falling within the any subregions underlying the current region.

Simultaneously, the minor profile m is updated in the regions where better information has been obtained. Only the updated minor profile m is stored in memory. The profile after being updated might read as follows:

| unknown | 6 | 7 | 7 | 7 | 8 | 10 | 12 | 14 | — |
|---|---|---|---|---|---|---|---|---|---|
| air | 0 | 0 | 0 | 0 | 0 | 0 | 0 | 0 | — |
| snow | 4 | 4 | 4 | 8 | 7 | 5 | 3 | 1 | — |
| ice | 4 | 4 | 4 | 2 | 1 | 0 | 0 | 0 | — |
| water | 1 | 0 | 0 | 0 | 0 | 0 | 0 | 0 | — |
| de-icing fluid | 0 | 0 | 0 | 0 | 0 | 0 | 0 | 0 | — |

This table indicates that there is some recognition that there is ice or snow over the surface, or perhaps an extremely thin layer of water. However, this recognition is quite tentative.

The table does confirm that the existence of de-icing fluid and the hypothesis that the sensor is clean have been rejected.

The process of boundary comparison, profile correction, and data structure selection is repeated until the relevant boundaries have been exhausted. The final sub-region in which the dithered data points fall might force the construction as follows:

| Distance | 0.1 | 0.2 | — | 1.8 | 1.9 | 2.0 | 2.1 | 2.2 | — |
|---|---|---|---|---|---|---|---|---|---|
| unknown | 0 | 0 | — | 0 | 0 | 0 | 0 | 0 | — |
| air | 0 | 0 | — | 0 | 6 | 9 | 15 | 15 | — |
| snow | 15 | 15 | — | 15 | 9 | 6 | 0 | 0 | — |
| ice | 0 | 0 | — | 0 | 0 | 0 | 0 | 0 | — |
| water | 0 | 0 | — | 0 | 0 | 0 | 0 | 0 | — |
| de-icing fluid | 0 | 0 | — | 0 | 0 | 0 | 0 | 0 | — |

In this example, the table indicates that the certainty that there is up to 1.8 mm of snow on the sensor is strong. The air-snow boundary occurs between 1.8 and 2.1 mm. The other material which could be overlying the sensor have been rejected.

The minor profile m is then added to the major profile M and the process is repeated for the next dithered test vector. The next dithered test vector will produce a second minor profile m. The minor profiles are then averaged by summation and subsequent shifting to produce a final major profile M. In this example the final major profile M might be as follows:

| Distance | 0.1 | 0.2 | — | 1.8 | 1.9 | 2.0 | 2.1 | 2.2 | — |
|---|---|---|---|---|---|---|---|---|---|
| unknown | 0 | 0 | — | 0 | 0 | 0 | 0 | 0 | — |
| air | 0 | 0 | — | 0 | 3 | 9 | 14 | 15 | — |
| snow | 15 | 15 | — | 15 | 12 | 1 | 0 | 0 | — |
| ice | 0 | 0 | — | 0 | 0 | 0 | 0 | 0 | — |
| water | 0 | 0 | — | 0 | 0 | 0 | 0 | 0 | — |
| de-icing fluid | 0 | 0 | — | 0 | 0 | 0 | 0 | 0 | — |

The result is then transferred to the display. The major profile M can be graphically displayed. Brighter shades correspond to higher degrees of certainty while lower shades to lesser certainty. Alternatively, the rows of the table can be integrated to display simply the existence or non-existence of a material overlying the sensor.

Figure 8:
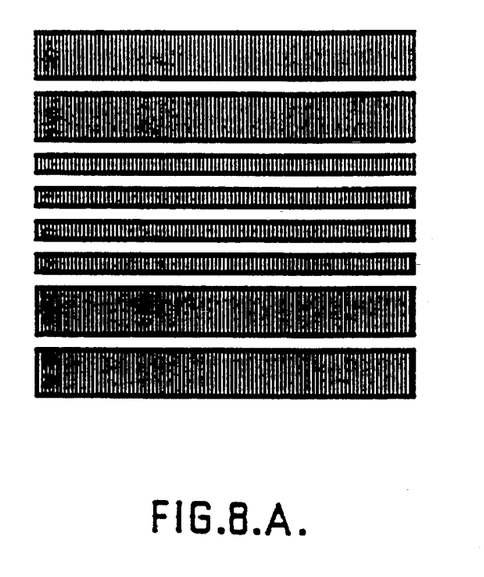
FIG. 8A–C are an illustration of alternate electrode configurations which may used in the embodiment of FIG. 1.

In the preferred embodiment, the geometry of the sensor electrodes is a plurality of concentric circular electrodes. FIG. 8 illustrates other possible electrode configurations which may be used.

An electrode arrangement must be designed such that it can be referenced by a standard co-ordinate system. For example, a set of parallel strip electrodes could be represented in rectangular coordinates. In this case, the discrete voltage pattern applied to the electrodes is a sine wave and the resulting pattern could be numerically represented by a Fourier series.

This option has inherent disadvantages over the concentric circular electrode system. A rectangular pattern of parallel electrodes would have to be represented in two dimensions unless the electrodes could be considered to be infinitely long. This would require additional complexity during the sensor design.

The preferred embodiment has been described in terms of a device and method for identifying and quantifying substances on an aircraft surface. However, it is apparent that the preferred embodiment could be used to identify and quantify any substance on any surface. For instance, such devices could be used to identify the relative make-up a flow of fluid through a pipe by installing a series of sensors about the pipe's inside surface.

In a second embodiment, a simplified map and mapping process may be used. The simplified map utilizes a number of contours which are representative of predetermined quantities of substances which may be overlying the sensor. By reducing the number of detectable substances, the speed of the mapping is greatly enhanced.

In general terms, the process of mapping the test vector to a region of the vector space can be accomplished using the following method. The analysis of a measurement set of the resulting currents is carried out in the following steps:

(a) generating a map means by projecting the boundaries of quantities of preselected substances onto coordinate planes in six dimensional space defining a plurality of contours, selecting about three contours which distinguishes one of the pre-selected substances from other substances and defining a contour set, each contour of the contour set is a closed polygon defined by a plurality of apex points corresponding to a quantity of one of preselected substances which may overly the sensor head, namely ice, snow or fluids and assigning each contour set with a priority value representative of the reliability of the generated contour set, where zero is representative of a pure boundary;

(b) Subdividing the map means into a predetermined number of levels;

(c) Inputting a data point comprising a raw measurement set to the on-board computer 20 from the sensor through communications system 18;

(d) Calibrating the raw measurement set by temperature calibration 72, and converting the measurement set to a vector format of three complex admittances in real and imaginary form for input to the interpretation routine 64;

(e) Summing the three complex admittances and comparing the result with a minimum threshold noise value, wherein, if the sum is less than or equal to the minimum value, then the data point represents a clean reading and a corresponding signal is generated;

(f) Calculating the amplitude of data point defined by the measurement set and identifying the level of the map means in which the amplitude of the data point falls;

(g) On the basis of the level, transforming and rotating the data point to an optimal coordinate system;

(h) Projecting the data point onto a coordinate plane defining a plurality of coordinates;

(i) Comparing the coordinates with each of the contour sets and if the coordinates is outside a contour of each of the contour sets, the data point represents a substance, which is other than snow, ice or fluid, if the coordinates is within each contour of only one of the contour sets then the data point represents the one substance, and if the coordinates is within each contour of more than one contour then the data point is considered to be within the contour set having the lowest priority value.

(j) generating a signal corresponding to the substance identified by the device.

More specifically, the mapping process of the second embodiment comprises the following steps. The input to the mapping routine of the second embodiment is the same vector DATA[n] which is a data set consisting of seven calibrated readings. Each reading is calibrated as previously outlined. The first six elements of the data set, sensor admittance readings, will be handled in a linear array, DATA[n],n=0, ... 5, and the temperature reading is designated as T.

The main database comprising the sample database 66 is used to create a simplified map comprising a plurality of boundary and profile functions in the manner previously discussed. The boundaries for predetermined quantities of ice, snow or fluids are determined. The mount of ice, snow or fluids represent quantities of such substances that would detrimentally affect the airflow characteristics of the aircraft surface.

The boundary functions for the quantities of ice, snow or fluids are projected into the six dimensional vector space to define a series of contours in a coordinate plane. About three contours are selected defining a contour set. Each contour are selected on the basis that the contours distinguishes one of the pre-selected substances from other substances and are of a convex shape. Each contour is a polygon having a plurality of apexes or pinnacles. Each contour set is assigned a priority value representative of the number of data points that are within a contour set which are not representative of that substance.

The map can further be subdivided by dividing the six dimensional space into a number of levels. In the preferred embodiment, the six dimensional space is divided into 32 levels between a clean sensor surface reading and a maximum amplitude value of the sensor. Each level will have an optimal coordinate system, depending on where the vector DATA[n] terminates within the six dimensional space. The optimal coordinate system positions the vector DATA[n] to a frame of reference where the vector DATA[n] is optimally distinguished from the contour sets. Each level will thus have a unique optimal coordinate system. The rotation and translation of the data to the optimal coordinate system is stored in a six by six array $R_{ijl}$ for rotating the vector DATA[n] and a linear array $F_{il}$ for translating the vector.

Contour sets $Q_{sl}$, where s is the substance and l is the level, are defined in each level for defining possible materials, such as snow, ice or fluid. It is possible that a contour set representing a particular material may not be present at a given level.

Each contour set, $Q_{sl}$, in a coordinate plane is a convex polygon represented by a series of apex points $U_i = (x_i, y_i)$, i=0, ... 15. The apex or pinnacles of the polygon, counted in counter clockwise direction, start at $U_{15}$ and end at $U_0$ where for a dosed polygon $U_{15} \equiv U_0$. Each contour set $Q_{sl}$ is assigned a priority that is equal to the number of data point which fall within the contour set which are not representative of the substance. A priority of zero indicates that a contour is pure. In other words, the database used to generate the contour set $Q_{sl}$ comprises only points of the indicated material which fall within the particular contour.

In use, the data from pattern A, B and C is preferably normalized in floating point format in the following manner.

$X_0 = Q_A \times DATA_0$ $X_1 = Q_A \times DATA_1$ $X_2 = Q_B \times DATA_2$ $X_3 = Q_B \times DATA_3$ $X_4 = Q_C \times DATA_4$ $X_5 = Q_C \times DATA_5$ where $Q_A$, $Q_B$ and $Q_C$ are predefined constants to normalize $X_n$ to a value of about 1.

The measurements are checked for a clean reading by summing the six reading and comparing the answer to a predefined value $c_o$, which is a minimum threshold noise value.

$$\sum_{i=0}^{5} |X_i| \leq c_o$$

If the sum is less than or equal to $c_o$ then the data point represents a clean reading and no further processing is required.

The amplitude of the data point, a, is calculated as follows:

$$\alpha = \sqrt{\sum_{i=0}^{5} X_i^2}$$

The amplitude a is sorted into one of preferably 32 levels designated l where l=0, . . . 31. A data point falls into a particular level, l if $$\frac{lM_{ax}}{32} < \alpha \leq \frac{(l+1)M_{ax}}{32}$$

where $M_{ax}$ is the maximum amplitude expected from the sensor.

The following steps are unique to each level, l. Each data point has a unique level so that only one level need be evaluated for a data point. Since the "volume" of the six dimensional space is reduced, computation time is reduced and identification speed is increased.

The data set $X_i$, i=0, . . . 5 is transformed into a new data set, $Y_j$, j=0, . . . 5 as follows, $$Y_j = \sum_{i=0}^{5} R_{ijl}(X_i - F_{il})$$

where $R_{ijl}$ is a six by six rotational array and $F_{il}$ is a six element linear translational array. Each level has an optimal coordinate system, depending on where the data point is with respect to the six dimensional space. Each level will thus have a unique optimal coordinate system.

The coordinates of $Y_j$, namely $(x_j, Y_k)$, j=0, . . . 5, k=0, . . . 5, j≠k generate the projection of the data onto the coordinate planes of the six dimensional space. The total possible number of independent projections is 15. On average, three independent projections $(x_j, y_k)$, $(x_{j'}, y_{k'})$, $(x_{j''}, y_{k''})$ corresponding to the coordinate planes on which the contour set $Q_{sl}$ are projected. The independent projections are checked to see if the data point falls within any contour set $Q_{sl}$ by forming the vector or cross product $$s = (U_{i+r} - U_i) \cdot (Y_p - U_i) = (x_{i+r} - x_i)(y_p - y_i) - (y_{i+r} - y_i)(x_p - x_i)$$

If for all i=0, . . . 15 the value of s is greater than zero (s>0) the data point is inside the contour set $Q_{sl}$. If for some value of i the value of s is less than zero the data point is outside the contour set $Q_{sl}$. For practical purposes the condition $s > -10^{-6}$ is used instead of s>0.

If the data point does not fall inside all three contours of all contour sets, the data point is declared to be in the "other" category. No further processing of this data point is required.

If the data point falls within all three contours of a contour set representing only a certain material the data point is declared to be that material. No further processing is required.

If a data point is inside more than all three contours of more than one contour set representing different materials, the data point is declared to be the material that has the lowest priority. No further processing is required.

Once the material overlying the sensor head has been identified, the interpretation routine 64 generates a signal corresponding to the material identified and computer and output 20 in response to the signal will generate an output signal identifying the substance.

It is to be understood that the scope of the present invention is not to be limited to the specific embodiments described above. The invention may be practised other than as particularly described and still be within the scope of the accompanying claims.

We claim:

1. An apparatus for identifying and quantifying in real time substances overlying a surface, the apparatus comprising:

a plurality of electrodes (26) underlying a surface, an electrode control means (14), connected to the plurality of electrodes (26), for applying a voltage pattern to the electrodes to define an electric field at the surface of a type which induces a plurality of currents in the electrodes which currents vary according to a substance overlying the surface, an amplitude and phase measurement means (16) connected to the plurality of electrodes (26) and to the electrode control means (14) for sensing a plurality of currents responsive to the electric field and converting the sensed currents to a measurement set, and computer means (20) having a memory and a processor, and display means responsive to an output signal for displaying the identity and quantity of substances overlying the surface, wherein the improvement is characterized by the memory having stored therein a map means of probable substances which could be overlying the surface, said map means being a partition of a vector space of predetermined characteristics of said probable substances into regions corresponding to an identity and quantity of said substances, said processor for correlating the measurement set with the partition of vector space in the map means thereby identifying and quantifying the substances overlying the surface and for generating an output signal corresponding to the identity and quantity of substances overlying the surface.

2. A method for identifying and measuring substances overlying a surface using a plurality of concentric electrodes (26) underlying a surface, an electrode control means (14) connected to the plurality of electrodes (26) for defining an electric field at the surface, an amplitude and phase measurement means (16) connected to the plurality of electrodes (26) and to the electrode control means (14) for measuring a plurality of currents responsive to the electric field, computer means (20) having a memory for storing a map means and a display means responsive to an output signal for displaying the identify and quantity of substances overlying the surface, the method comprising the steps of:

(a) applying an electric field at the surface, (b) measuring a plurality of currents responsive to the electric field, (c) converting the currents to a measurement set, and (d) correlating the measurement set with the map means thereby identifying and quantifying the substances overlying the surface, and (e) generating an output signal corresponding to the identity and quantity of substances overlying the surface, wherein the improvement is characterized by said map means being generated by projecting boundaries between preselected quantities of probable substances onto coordinate planes in six dimensional space and selecting a contour set of about three closed convex contours, each of which distinguishes one of the preselected quantities of probable substances from other substances, and assigning each contour set with a priority value representative of the reliability of the contour set, where zero is representative of a pure boundary.

3. A method as claimed in claim 2 wherein said map means is subdivided into a predetermined number of levels.

4. A method as claimed in claim 3 wherein said computer means calibrates and scales the measurement set to a vector of three complex admittances in real and imaginary form.

5. A method as claimed in claim 4 wherein the computer means sums the vector and the summation is compared with a minimum threshold noise value, wherein, if the summation is less than or equal to the minimum value, then the measurement set represents a clean reading and a corresponding output signal is generated.

6. A method as claimed in claim 5 wherein said computer means calculated the amplitude of the measurement set and identifies the level of the map means in which the amplitude falls; on the basis of the level, said computer means transforms and rotates the measurement set to an optimal coordinate system; said computer means projects the measurement set onto a coordinate plane defining a plurality of coordinates and compares the coordinates with each of the contour sets and if the coordinates is outside a contour of each of the contour sets, the measurement set represents a substance, which is other than one of preselected quantities of probable substances if the coordinates is within each contour of only one of the contour sets then the data point represents the one substance, and if the coordinates is within each contour of more than one contour then the data point is considered to be within the contour set having the lowest priority value.

7. An apparatus as claimed in claim 2 wherein said map means is a selection of a contour set comprising about three closed convex contours, each of said contours being a projection of a plurality of boundaries between preselected quantities of probable substances onto coordinate planes in six dimensional space and which distinguishes one of the preselected quantities of probable substances from other substances, and an assignment of each contour set with a priority value representative of the reliability of the contour set.

8. An apparatus as claimed in claim 7 wherein said map means is subdivided into a predetermined number of levels.

9. An apparatus as claimed in claim 8 wherein said computer means calibrates and scales the measurement set to a vector of three complex admittances in real and imaginary form.

10. An apparatus as claimed in claim 9 wherein the computer means sums the vector and the summation is compared with a minimum threshold noise value, wherein, if the summation is less than or equal to the minimum value, then the measurement set represents a clean reading and a corresponding output signal is generated.

11. An apparatus as claimed in claim 10 wherein said computer means calculates the amplitude of the measurement set and identifies the level of the map means in which the amplitude falls; on the basis of the level, said computer means transforms and rotates the measurement set to an optimal coordinate system; said computer means projects the measurement set onto a coordinate plane defining a plurality of coordinates and compares the coordinates with each of the contour sets and if the coordinates is outside a contour of each of the contour sets, the measurement set represents a substance, which is other than one of preselected quantities of probable substances if the coordinates is within each contour of only one of the contour sets then the data point represents the one substance, and if the coordinates is within each contour of more than one contour then the data point is considered to be within the contour set having the lowest priority value.

* * * * *